United States Patent
Costello, III et al.

(10) Patent No.: US 8,066,961 B2
(45) Date of Patent: Nov. 29, 2011

(54) KINEMATIC WELLPLATE MOUNTING METHOD

(75) Inventors: John J. Costello, III, Painted Post, NY (US); Martin J. Popoloski, Woburn, MA (US); John C. Thomas, Elmira, NY (US)

(73) Assignee: Corning Incorporated, Corning, NY (US)

( * ) Notice: Subject to any disclaimer, the term of this patent is extended or adjusted under 35 U.S.C. 154(b) by 1117 days.

(21) Appl. No.: 11/454,766

(22) Filed: Jun. 15, 2006

(65) Prior Publication Data
US 2007/0020152 A1 Jan. 25, 2007

Related U.S. Application Data

(60) Provisional application No. 60/701,452, filed on Jul. 20, 2005.

(51) Int. Cl.
*B01L 9/00* (2006.01)
(52) U.S. Cl. ......... 422/560; 422/551; 422/553; 422/561
(58) Field of Classification Search .............. 422/99, 422/102, 104, 551, 552, 553, 560, 561, 566
See application file for complete search history.

(56) References Cited

U.S. PATENT DOCUMENTS

| | | | |
|---|---|---|---|
| 4,971,514 A | 11/1990 | Hunter | |
| 5,487,384 A | 1/1996 | Lee | 128/633 |
| 5,592,289 A | 1/1997 | Norris | 356/244 |
| 5,705,331 A | 1/1998 | Arthur et al. | 435/5 |
| 5,763,199 A | 6/1998 | Coller | 435/721 |
| 5,854,005 A | 12/1998 | Coller | 435/7.21 |
| 5,932,418 A | 8/1999 | Yager | 435/6 |
| 6,027,694 A | 2/2000 | Boulton et al. | 422/102 |
| 6,228,345 B1 | 5/2001 | Ossowski | 424/9.1 |
| 6,500,390 B1 | 12/2002 | Boulton et al. | 422/100 |
| 6,635,416 B2 | 10/2003 | Palese et al. | 435/5 |
| 6,755,131 B2 | 6/2004 | Dannoux et al. | 101/485 |
| 2002/0037237 A1 | 3/2002 | Mainquist et al. | 422/63 |
| 2003/0017083 A1 | 1/2003 | Pobering et al. | |
| 2003/0205511 A1 | 11/2003 | Olivier et al. | 210/95 |
| 2004/0065793 A1 | 4/2004 | Shelef | 248/181.1 |
| 2004/0239922 A1 | 12/2004 | Modlin | |
| 2005/0136534 A1 | 6/2005 | Austin et al. | 435/287.2 |

FOREIGN PATENT DOCUMENTS

| | | |
|---|---|---|
| DE | 201 01 080 | 6/2002 |
| EP | 1358937 * | 5/2003 |
| WO | WO 96/21855 | 7/1996 |
| WO | WO 99/20394 | 4/1999 |

* cited by examiner

*Primary Examiner* — Jill Warden
*Assistant Examiner* — Dwayne K Handy
(74) *Attorney, Agent, or Firm* — Gregory B. Butler; Thomas R. Beall

(57) ABSTRACT

A mechanism for positionally restraining a microplate is disclosed. The mechanism is defined by a base having at least one surface with a receptacle for the insertion of a microplate into the base. Supports and/or positioning structures on a surface of the base have point contacts to restrain movement of the microplate in a stable position for repeatable optical detection measurements. The supports and/or positioning structures permit insertion of the microplate for an initial measurement, removal of the microplate for analytical manipulation, and re-insertion of the microplate to an exact position so as to allow analysis of precise comparative measurements by an optical reader.

20 Claims, 12 Drawing Sheets

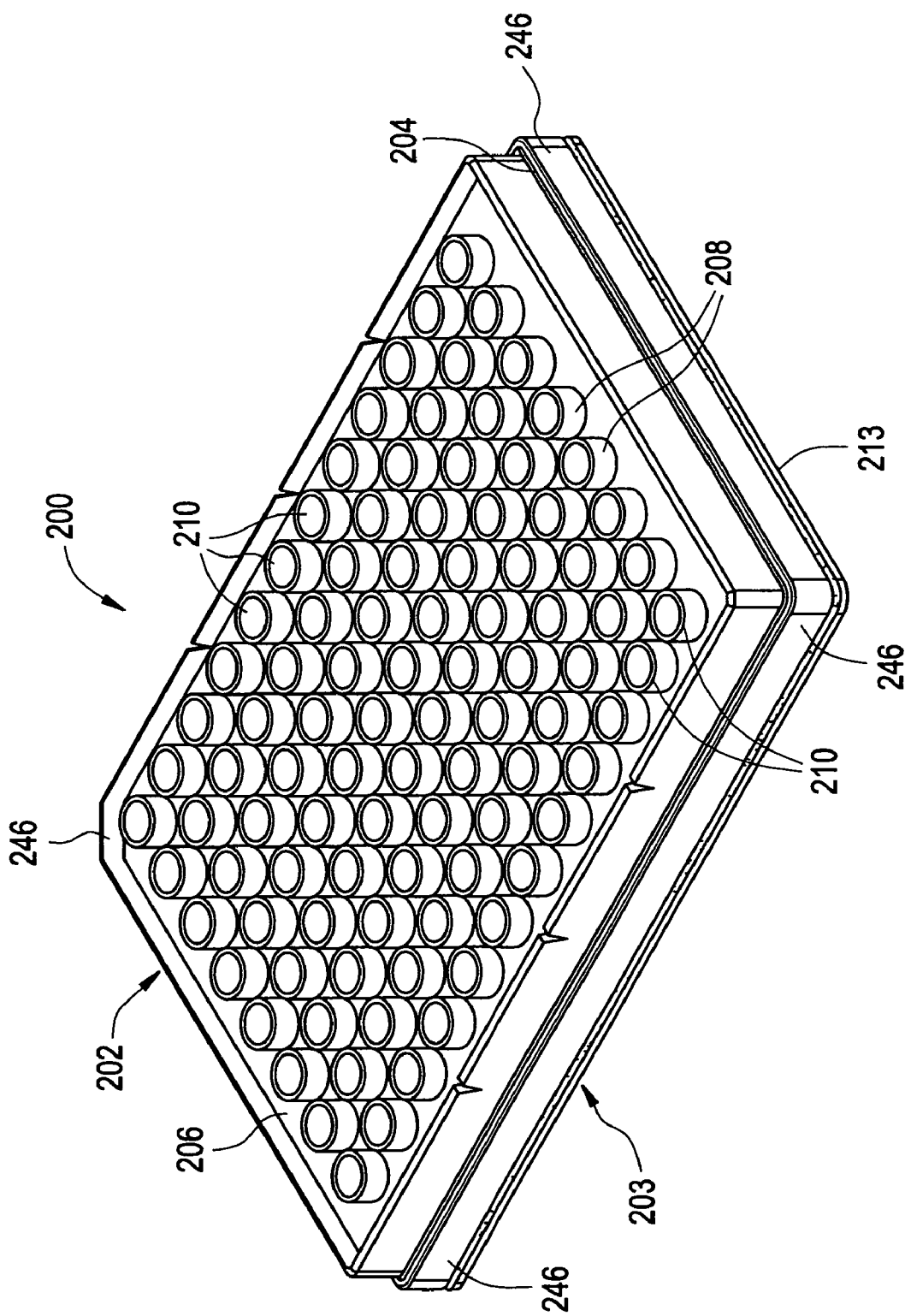

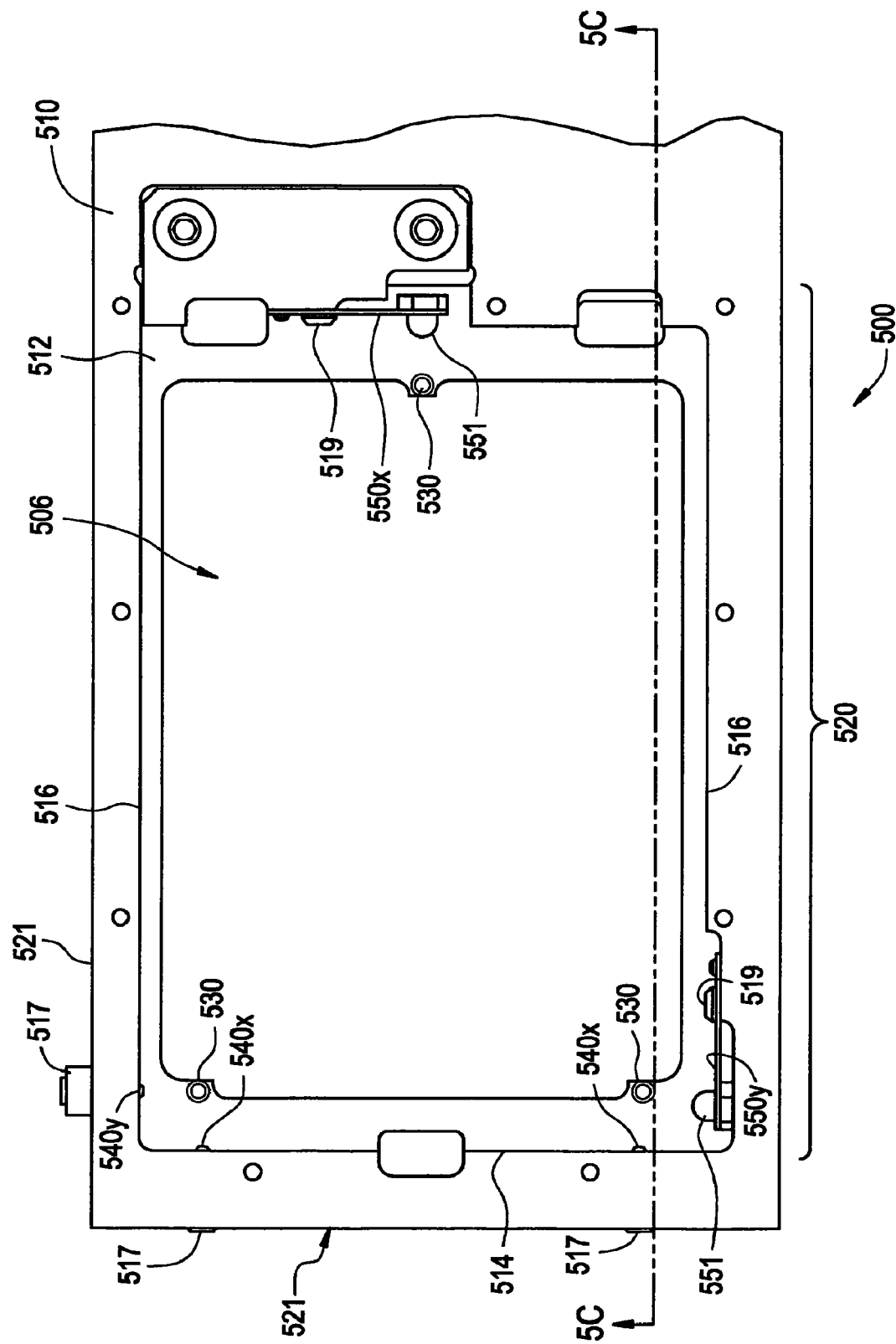

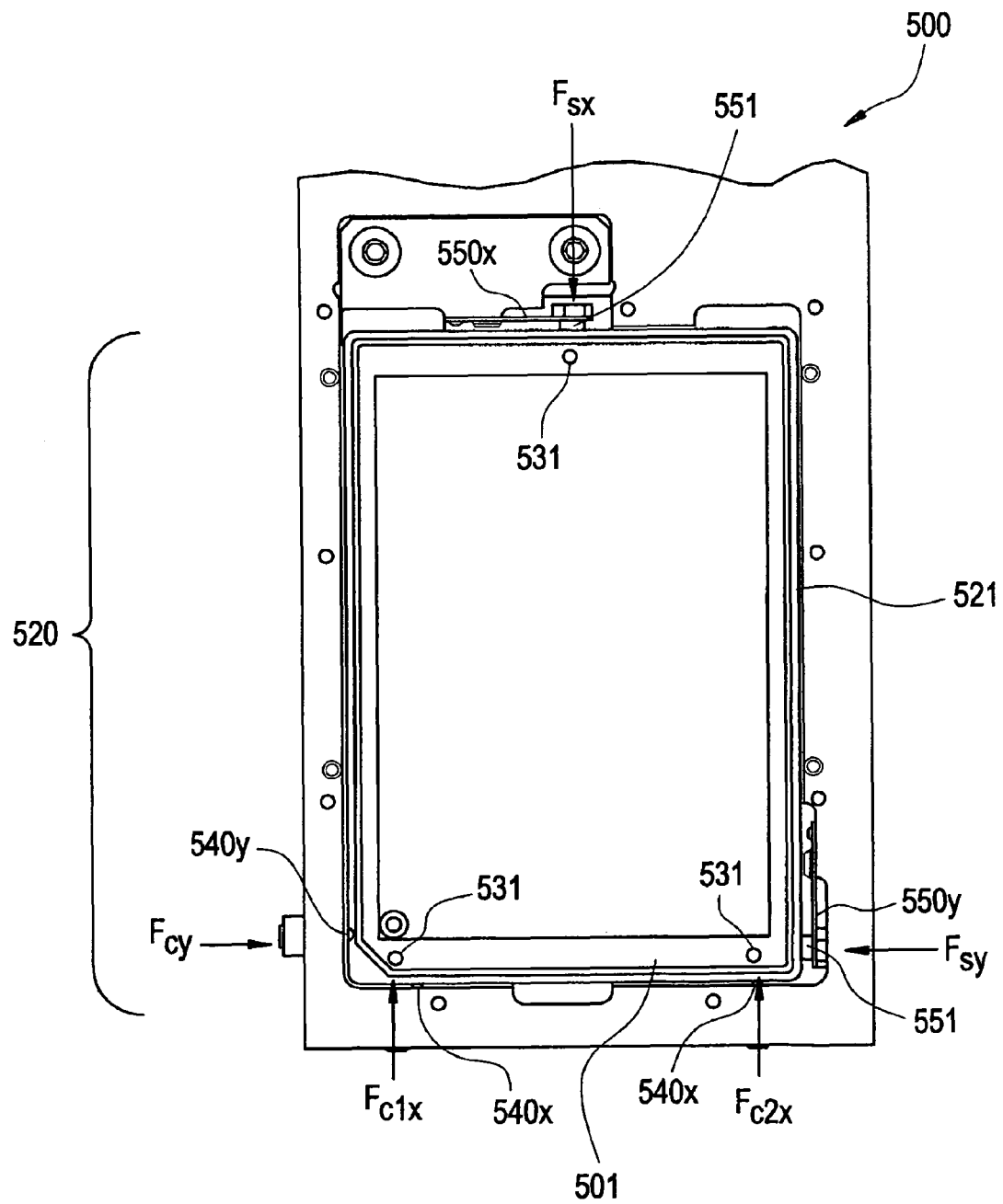

KINEMATIC WELLPLATE MOUNTING METHOD

CROSS-REFERENCE TO RELATED APPLICATIONS

This application claims the benefit of U.S. Application Ser. No. 60/701,452 filed on Jul. 20, 2005 and entitled "Kinematic Wellplate Mounting Method" which is incorporated by reference herein in.

FIELD OF THE INVENTION

The present invention relates generally to a mechanism for restraining a microplate in a fixed position.

BACKGROUND OF THE INVENTION

At the present time, existing technology utilizes various instrumentation to measure photometric properties such as color, absorbance, intensity, and photoluminescence at specific locations on a microplate surface where chemical and biological samples are associated. For example, optical readers are commonly used in biological fields such as genetic research, drug discovery, or diagnostic purposes to detect hundreds or thousands of compounds (e.g., DNA, oligonucleotides, proteins, etc.) typically deposited on a surface of a substrate (e.g., a glass slide) in an array configuration. It is well known in the art that proper alignment of the microplate holding the samples and the light beam of the optical device is necessary to perform many photometric measurements.

Similarly, to perform image analysis, devices such as optical scanners/readers and microscopes demand sample stages that provide consistent and accurate positioning of the microplate. Moreover, for imaging devices that utilize sensors, waveguide gratings or other microdevices on a sample surface of a substrate, alignment of the surface having correlation with an optical component is critical for consistent measurements.

Many photometric instruments make use of a multi-site microplate to prepare a large number of test samples. Microplates are typically rectangular structures made of glass or plastic, each having a plurality of wells for holding sample material. The plate itself is generally inexpensive, safe, sturdy, and convenient to handle. They are disposable, but can be cleaned easily and may be reused when necessary.

As chemical and biological sample size decreases and the number of samples increases on an array surface, alignment of the samples relative to the measuring instrument becomes progressively more important. Present and future drug discovery relies on a large number of test sites within an array. For example, to identify a specific protein sequence for a binding event with a certain type of receptor, a high density of samples is needed to expose the receptor to as many different permutations of proteins as possible. Therefore, the samples to be assayed are located on the surface in a multitude of discrete locations, each location containing a single sample. A standard microplate is typically about 127.76 mm in length×85.48 mm in width and may accommodate up to 384 or even 1536 assays. Because of the small size and close spacing of the analyte samples, the microplate sample surface must be precisely and repeatably aligned with respect to the measuring apparatus, thus allowing the measuring apparatus to make error-free measurements of the samples.

Systems are currently being developed to detect the binding of molecular species without adding labels. These systems utilize disposable microplates having sensors embedded at specific locations and a reader to interrogate those precise localities of the microplate. The utility of assays performed in such systems relies on making successive analytical observations interplayed between steps in the assay. This way, a true "before and after" analysis may be accomplished revealing the occurrence (or absence) of biological or chemical molecular interactions. Therefore, the repeatable and consistent alignment and/or positioning of a microplate incorporated into or onto a stage for analytical interrogation is crucial and necessitated by these newly developed systems.

Current measurement protocol requires four primary steps: (1) initial/background measurement, (2) removal of the plate (for additional assay steps), (3) reinsertion of the plate into the reader, (4) second measurement, and (5) comparison of first and second measurements. Following the placement of a microplate into an exact location, an initial measurement can be read by a photometric/optical instrument. Once the microplate is removed, and manipulation of its contents completed, examination of the microplate depends on the exact repositioning of the microplate into the reader. Therefore, the second/final measurement result can be adversely affected by the slightest change, rotational and/or translational, in microplate position between the initial and second/final measurement steps.

There is a need for a mount that will reduce the range of motion required in active repositioning of a microplate. In addition, it is desirable to have a mechanism that may limit any freedom of motion of a microplate while restrained in X, Y, and Z planes. The mechanism would also provide consistent and reproducible positioning of a microplate in a location upon successive mounts. Depending on the assay and the detection equipment, it may be necessary that successive positioning of a microplate within a stage not vary by more than 1 micron translation or 20 microRadians rotation. Furthermore, a mount design capable of allowing possible robotic manipulation of the microplate would be beneficial to future high-throughput analysis.

SUMMARY OF THE INVENTION

One aspect of the invention relates to a mechanism for positionally restraining a microplate including a base having at least one surface defining a nest or nesting receptacle for a microplate, and at least three supports that project from the surface of the base and are capable of supporting a microplate. The nesting receptacle of the claimed mechanism has at least two side walls and at least two end walls that intersect in corners to form a rectangular shape in which the walls define a detection aperture allowing optical accessibility to at least one surface of the microplate through the detection aperture. The supports of the mechanism have any rigid composition, nonreactive materials such as metals, carbide, diamond, or ruby being preferable.

In another embodiment of the present invention, the mechanism may further comprise a precision assembly in which the base is secured to an assembly that is capable of moving the nesting receptacle into and out of view of an optical reader. A preferred embodiment of this invention includes an alignment system wherein the nesting receptacle holding a microplate may be precisely positioned to a location above an optical reader/detector so that the microplate sample surface can be repeatably inserted into the nesting receptacle in an analogous first and second location, each location situated respective to one another within less than about 1 micron translation and less than about 20 microRadians rotation. It is even more preferable to have the second location of the positioned microplate within less than about 15 microRadians rotation (smaller numbers being more confining) of first location.

Another embodiment of the present invention is a microplate restraining mechanism whose supports contain one or more mating features that are capable of interacting with one or more respective microplate mating feature(s). The mechanism may additionally exhibit one or more guide pins located on a periphery or outer edge of the nesting receptacle. These guide pins are capable of aligning a microplate into a predefined position with respect to the supports. As such, a preferred embodiment of the mechanism of the present invention has one or more pair(s) or set(s) of guide pins located on the corners or sides of the nesting receptacle such that the guide pins are capable of aligning at least one microplate side or corner. Guide pins may be advantageous in manual or robotic movement and manipulation of the microplate to assist in precise positioning of the microplate. The guide pins are preferably shaped to assist in the gradual positioning of the microplate such that sudden movements of the microplate are avoided further preventing disruption of the contents on the microplate sample surface(s). Though any shape or combinations of shapes are suitable, a preferred embodiment has guide pins with a cylindrical shaped base at a point of attachment on the periphery of the nesting receptacle. The cylindrical shape tapers upward to a conical shape where a microplate is capable of being initially received.

In another aspect, the present invention includes a microplate comprising a substantially flat transparent lower plate having at least one bottom surface or multiple bottom surfaces for an array of sample wells. A unitary upper plate may form the sidewalls for the sample wells. A frame of the microplate surrounds the array of sample wells. The preferred frame has one or more microplate mating feature(s) located on an underside surface which are capable of interacting with one or more supports projecting from a base of a restraint mechanism.

In another aspect, the present invention includes a microplate assembly comprising a restraint mechanism having a base with at least one surface defining a nesting receptacle for a microplate, at least three supports projecting from the base to support the microplate, and a microplate located within the nesting receptacle contacting the supports. In one embodiment of the present invention, at least six constraints are utilized in order to maintain positional stability of the microplate in the X, Y, and Z planes; three microplate mating features contact/engage with three mating features of the supports generating six point contacts between the microplate and the base of the restraint mechanism. The microplate of this assembly is further capable of comprising at least one well having at least one sensor located within a bottom surface of the well.

In another embodiment of the present invention, the supports project from one or more secondary surface(s) of the restraint mechanism in the absence of specific mating features. The secondary surface is preferably inset on the end walls and side walls of the nesting receptacle further forming a ledge on a periphery of the detection aperture. In addition, the supports can include one or more point contact(s) capable of contacting at least one underside surface of a microplate. In this alternative embodiment, three supports are utilized on the secondary surface and a plurality of positioning structures are located on the end walls and side walls to further restrain a microplate in a fixed location. A minimum of six point contacts must be provided in order to constrain the six degrees of freedom. More contacts may be required to provide a preload force into the contacts provided. One such embodiment includes at least one X-directional contact and at least one Y-directional contact on respective end and side walls; the end wall having the X-directional contacts is perpendicular to the side wall having the Y-directional contact. Preferably, the mechanism comprises at least two X-directional contacts and at least one Y-directional contact located on said end walls and side walls, respectively, in addition to at least one spring-loaded contact on said end wall opposite said X-directional contact and at least one spring-loaded contact on said wall opposite said Y-directional contact.

In addition, an embodiment of the mechanism of the present invention is shaped and configured to enable robotic access to the microplate mount/stage area, where the microplate is positioned into the base without requiring cumbersome robotic arm manipulation.

The present invention also includes a method for positionally restraining a microplate in a fixed location within an optical detection system. The method initially involves providing a restraining mechanism as previously described in cooperation with an analytical system such as an optical detector or optical detection system. Other instrumental systems (ie. dispensing units) may be incorporated as well in manipulation or analysis of the microplate. A microplate is initially inserted to occupy a first defined location of the nesting receptacle whereby a detection system can record an initial first measurement(s) of the microplate. Subsequently, the microplate is removed from the nesting receptacle. The reinsertion of the microplate within the nesting receptacle establishes a second defined location with respect to the analytical system, such that the difference in position between the first location and the second location is less than about 1 micron in translation and less than about 4 arc seconds (preferably, less than 3 arc seconds is more confining) or 20 microRadians rotation (preferably less than about 15 microRadians rotation). The optical detection system can then record a second measurement of the microplate sample surface(s) at this second defined location so as to make a comparable analysis with the initial reading at the first defined location.

It is accordingly desirable to provide a mechanism that reduces the range of motion required in active repositioning of a microplate. Moreover, it is desirable to have a mechanism that limits the movement of the microplate while restrained in X, Y, and Z planes of a defined position upon successive mounts. It is further advantageous for the microplate restraining mechanism to be consistent and reproducible. Depending on the assay and the detection equipment, it may be desireable that successive positioning of a microplate within a stage not vary by more than 1 micron translation or 20 microRadians rotation. Furthermore, a mount design capable of allowing possible robotic manipulation of the microplate is beneficial to future high-throughput analysis. Additional advantages of the invention will become apparent after consideration of the ensuing description and the accompanying drawings.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

FIG. 2 is an illustrative embodiment of a microplate sample surface containing an array of wells.

FIG. 5A is an enlarged top view of a nesting receptacle of FIG. 5.

FIG. 5E is a top view of a microplate nested in the restraint mechanism demonstrating applicable forces.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
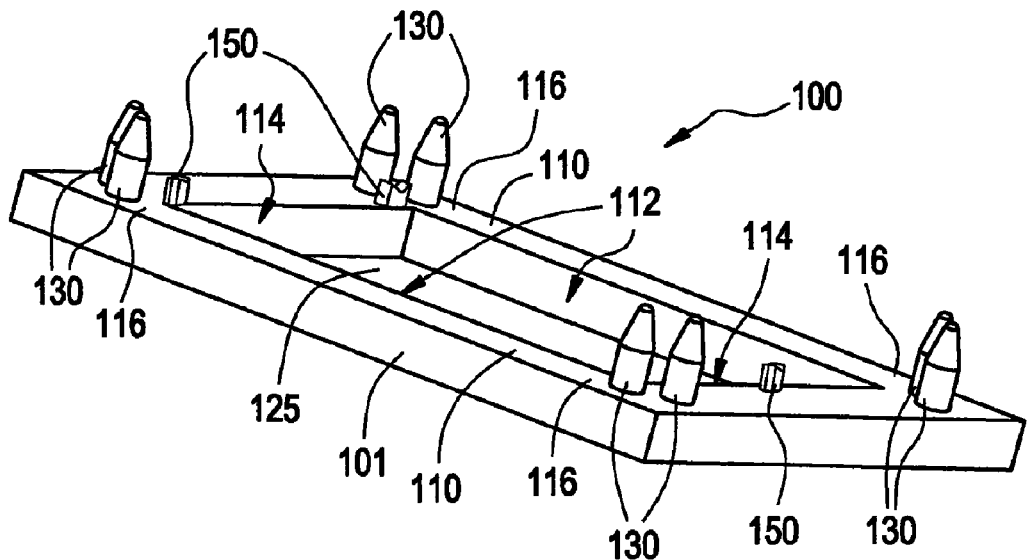
FIG. 1 is a perspective view of an illustrative embodiment of the restraint mechanism of the present invention.

The restraining mechanism 100 in accordance with one embodiment of the present invention is illustrated in FIG. 1. The mechanism 100 comprises a structure/base 101 having a surface 110, as well as three supports 150 projecting from the base 101 which are capable of supporting a microplate. Two side walls 112 and two end walls 114 intersect in corners 116 to form a rectangular periphery having an opening or a detection aperture 125. The detection aperture 125 allows an optical detector located under the mechanism to directly access wells of a microplate located and rested within the mechanism 100. The mechanism 100 further has sets of guide pins 130 located on the surface 110 of the base 101, preferably near the detection aperture 125. The pairs of guide pins 130 in each corner 116 allow a microplate to be positioned gradually in a location within the mechanism 100 to align with the supports 150.

Figure 1A:
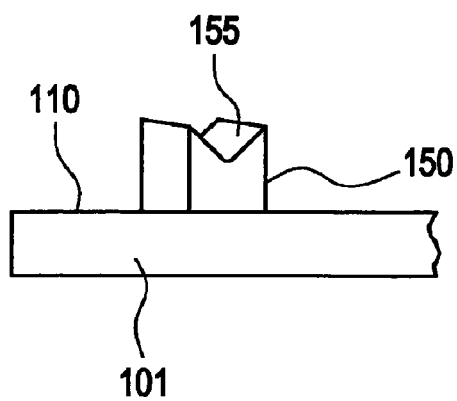
FIG. 1A is a magnified illustration of a V-shaped mating feature of the present invention.

One aspect of the invention relates to a restraining mechanism 100 having supports 150 comprising mating features 155 in V-shapes (as magnified in FIG. 1A). In this preferred embodiment, the mating features 155 are mating surfaces 155 incorporated within the supports 150. Three supports 150 having mating surfaces 155 attach to the base 101 and are arranged on the surface 110 to support a microplate. The supports 150 are intended to be constructed having hard, rigid attributes such as material compositions including ceramic, metallic, or carbide materials. The mating feature is designed to interact in a stabilized manner with an opposing mating feature on a microplate. Two of the supports 150 are located on a corner 116 angled toward the centroid of the detection aperture 125 and one support 150 is located on (and parallel to the centroid axis that passes between the two supports 150 and the centroid of the detection aperture 125) on an opposite end wall 114. The supports 150 are attached to the base 101, respective to one another, so that a microplate is capable of being restrained with limited movement, specifically less than about 1 micron translation in the X or Y directions and less than about 4 arc seconds (again, smaller numbers are more confining) or less than about 20 microRadians (preferably less than about 15 microRadians) rotation about the Z directional axis.

Figure 1B:
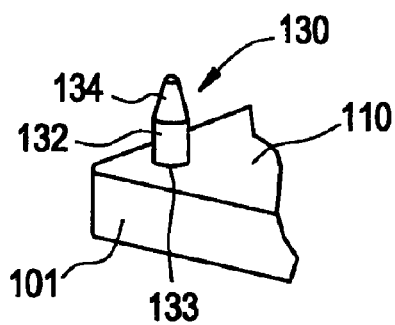
FIG. 1B is a magnification of a guide pin from a restraint mechanism of the present invention.

In addition, another aspect of the present invention relates to the guide pins 130 attached to the base 101, preferably shaped with capability to assist in the gradual positioning of a microplate. Though any shape or combination of shapes are suitable, this preferred embodiment has a set of guide pins 130, each having a cylindrical shaped base 132 at a point of attachment 133 on a surface 110 of the base 101. In this embodiment, the cylindrical shape 132 tapers upward to a conical shape 134 where a corner of a rectangular shaped microplate is capable of being initially received (See FIG. 1B). If utilized, however, the guide pins 130 can be located anywhere on the base 101, not necessarily in a corner location. The structure of the supports 150 and guide pins 130 can be achieved by integrally incorporating the structures into the molding process or by attachment using any chemical adhesive (i.e. epoxy) or mechanical process (i.e. welding). The location within the restraint mechanism upon which the microplate is securely supported defines the nesting receptacle. In this embodiment, the portion of the top surface defining a periphery of the detection aperture, in cooperation with the guide pins and supports, make up the nesting receptacle. (Referring to FIG. 3A, the microplate fully occupies the nesting receptacle 303.) Furthermore, the supports 150 and guide pins 130 of the mechanism 100 may have any rigid composition, though hard, nonreactive materials (carbide, metallic, diamond, etc.) are preferable.

Figure 2A:
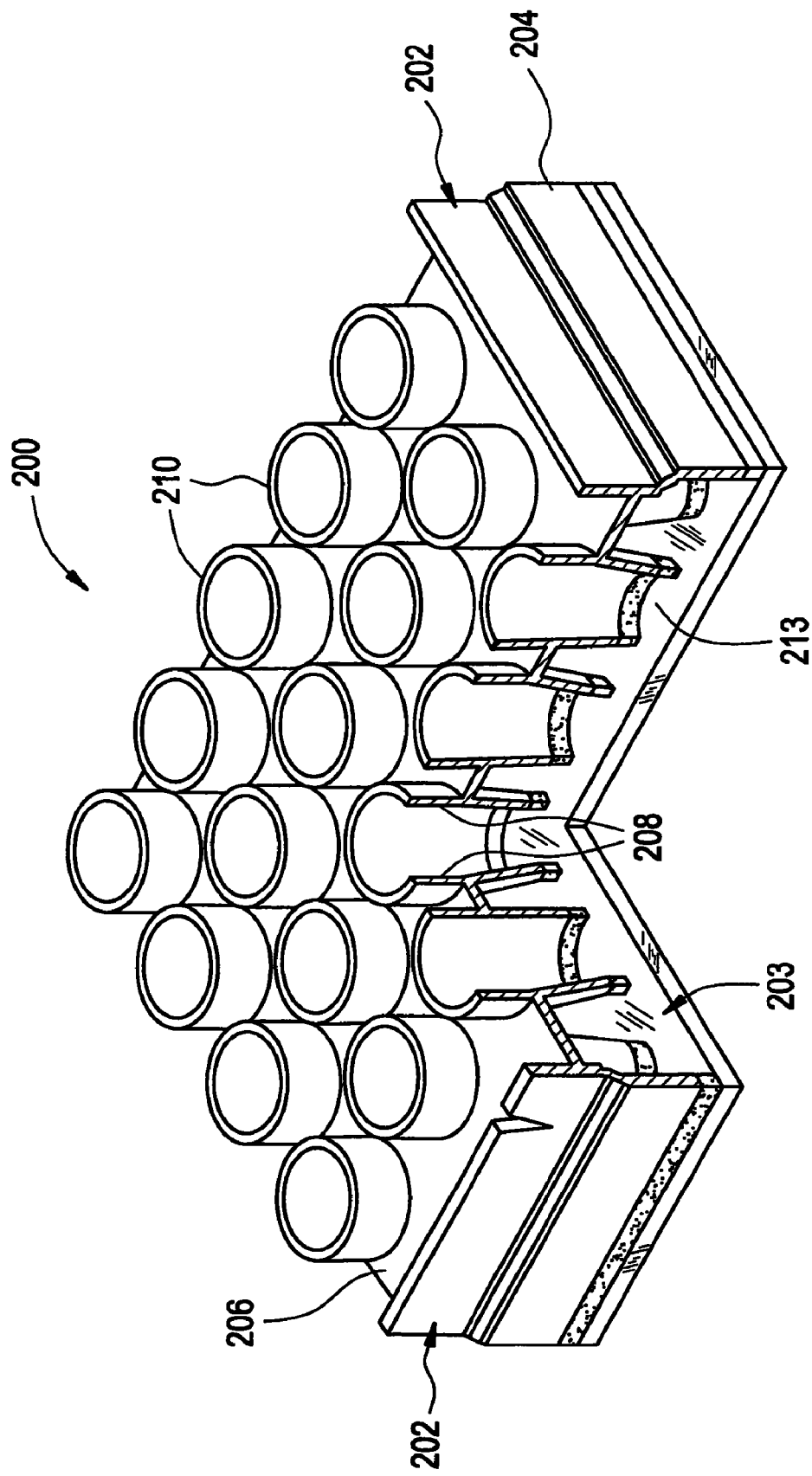
FIG. 2A is a partial cutaway section of the array of wells from FIG. 2.
Figure 2B:
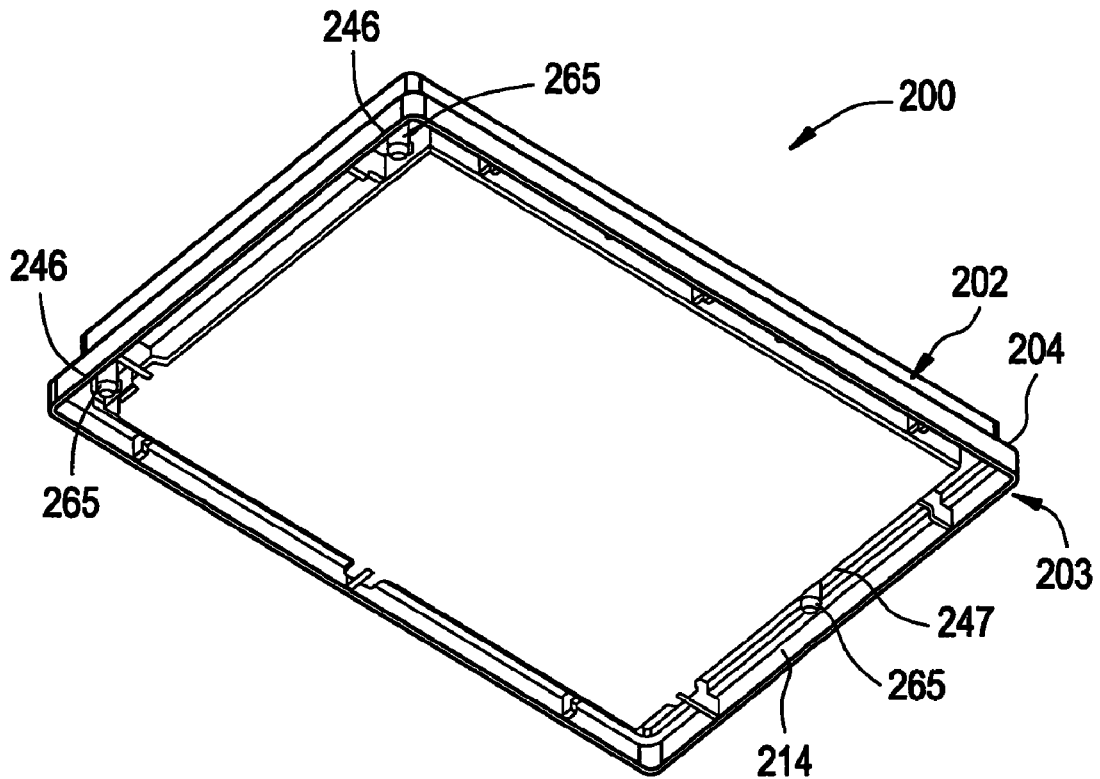
FIG. 2B is an underside 3-dimensional view of a microplate of the present invention.
Figure 2C:
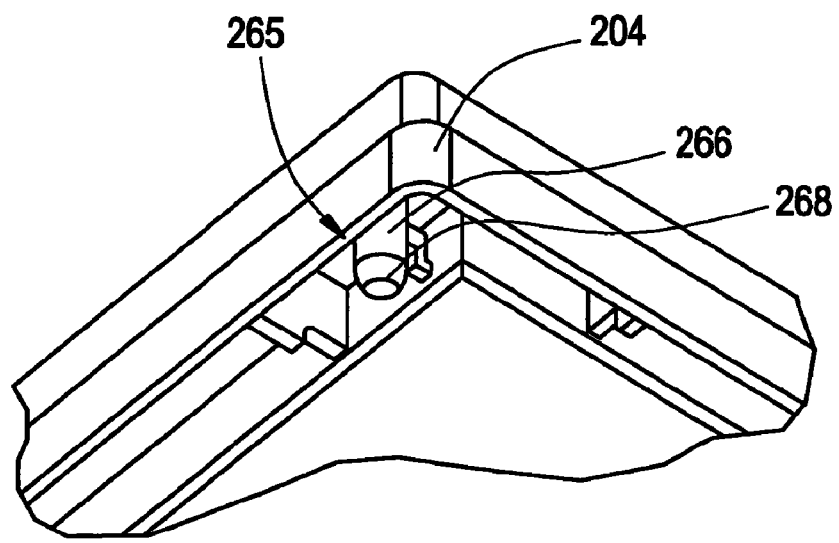
FIG. 2C is an enlarged perspective view of a microplate mating feature of the present invention.

A microplate 200 (e.g., multiwell plate), capable of being positioned in a restraining mechanism 100, is illustrated in FIG. 2. The microplate 200 having an array of wells 210 is typically of two-part construction including an upper plate 202 and a lower plate 203. The upper plate 202 includes a peripheral skirt/frame 204, a top surface 206, and sidewalls 208 to delineate the array of the wells 210, each well 210 capable of receiving an aliquot of sample to be assayed. The lower plate 203 forms a substantially and preferably flat transparent bottom wall/surface 213 (as seen in FIG. 2A) for each sample well 210 in which an optical detector located under the microplate 200 has direct access to the array of wells 210. The sensor can detect activity occurring within the wells or, alternatively, on the bottom surface of the well. In one embodiment, the plate has a biological sensor or grating/waveguide optical configuration located within the bottom of at least some of the wells.

Additionally, the microplate 200 preferably has three microplate mating features/structures 265 protruding from an underside surface 214 (FIG. 2B) and capable of aligning with three mating features of a restraint mechanism. The microplate mating features 265 are preferably located in a configuration to stably support the microplate 200; specifically, two mating features 265 are located in proximity to one end wall in two respective corners 246 and one mating feature 265 proximate to the opposing end wall 247. The microplate mating features 265 in this preferred embodiment of the modified microplate 200 are cylindrical structures 266 (FIG. 2C) having spherical mating points 268 capable of point contacting each mating feature of a restraint mechanism for a total of six point contacts.

Preferably, the microplate 200 conforms to industry standards for microplates; that is to say, the microplate 200 is bordered by a peripheral skirt 204, laid out with preferably 96 (mutually perpendicular rows of 8 and 12) wells 210, 384 sample wells (mutually perpendicular 16 and 24 well rows), and up to 1536 wells (perpendicular 32 and 48 well rows). In addition, the height, length, and width of the microplate 200 preferably conform to industry standards. However, the present invention can be implemented in a microplate that has any number of wells and is not limited to any specific dimensions and configurations. Other known and commercially available microplate designs can work just as well including those having opaque and/or one-piece molded surfaces.

Figure 3:
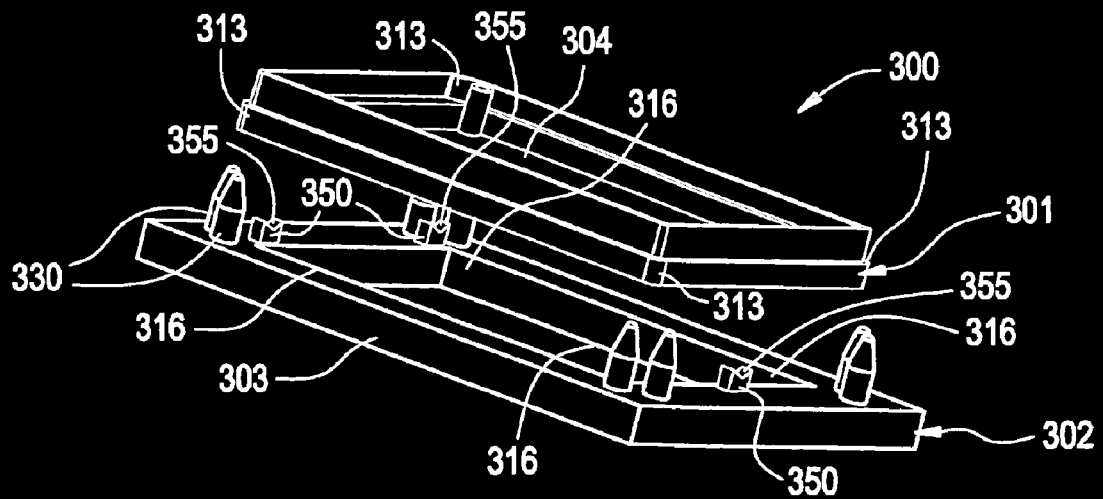
FIG. 3 is a perspective view of a microplate assembly of the present invention.
Figure 3A:
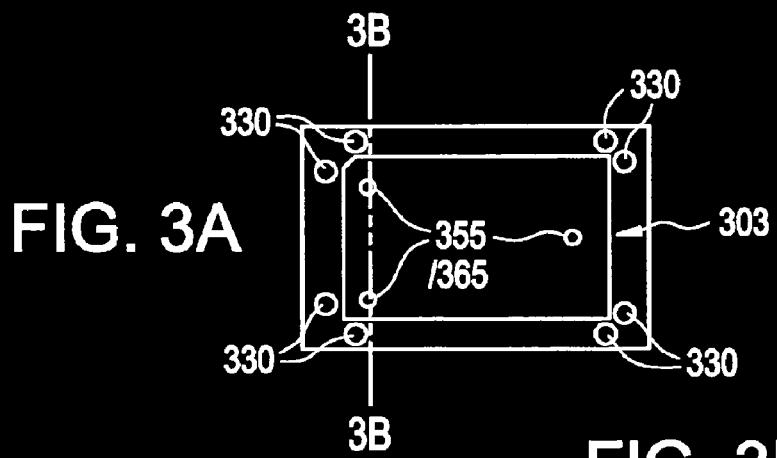
FIG. 3A is a transparent top view of the microplate assembly of FIG. 3.
Figure 3B:
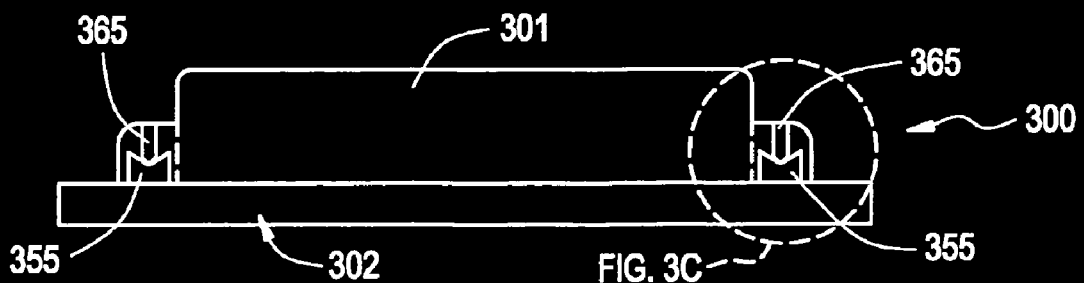
FIG. 3B is an enlarged cross-sectional view of FIG. 3, across section line a-a.
Figure 3C:
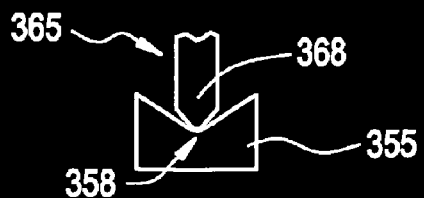
FIG. 3C is a magnification of the engaged mating features from corner 309 of FIG. 3B.

FIG. 3 illustrates one embodiment 300 of the present invention showing a microplate 301 positioned above the mechanism 302. Preferably, the restraint mechanism 302 of the present invention has four pairs/sets of guide pins 330 located on each of the corners (or sides) 316 such that each set of guide pins 330 are capable of aligning each of the four microplate corners 313. Guide pins 330 are advantageous in manual or robotic movement and manipulation of the microplate 301 to assist in restraining the microplate 301. The corners 313 are situated to align the three supports 350 having V-shaped mating features 355 with three corresponding spherical point contact microplate mating features 365 of the microplate 301 (as seen in a transparent top view of a microplate 301 engaged with the mechanism 302 in FIG. 3A). A sectional cut across line 3B-3B in FIG. 3A provides a cut away cross-section shown in FIG. 3B further illustrating the detail of two of the three microplate mating features 365 engaged with two of the three corresponding mating features 355 of the restraint mechanism 302. The cylindrical microplate mating feature 365 is engaged with the V-shaped mating feature 355 of the restraint mechanism 302. Specifically, FIG. 3C demonstrates spherical point contacts 368 of the microplate mating structures 365 interacting with the three contact points 358 within the V-shaped mating features 355 of the restraint mechanism 302. Thus, when three microplate mating structures 365 engage with three mating features 355, a total of six contact points constrain movement of the microplate 301. According to well-known principles, for a rigid body to be completely fixed in space, despite disassembly and reassembly, all six degrees of freedom need to be constrained. In other words, three translations and three rotations must be constrained with respect to some arbitrary fixed coordinate system. A mount is said to be kinematic when all six degrees of freedom are constrained. A kinematic mount therefore has at least six independent constraints or points of contact. As such, it is preferred that the restraint mechanism of the present invention be capable of a kinetic mount. However, any number of mating structures 355 and microplate mating structures 365 may provide a stable configuration to restrain the microplate 301. As such, the number of contact points will depend on the total number of mating structures 355 and microplate mating structures 365.

The mating features 355 and microplate mating features 365 allow for the positioning and repositioning of the microplate 301 following manipulation such as addition or removal of chemical and biological analytes to the sample surfaces 304 of the microplate 301. The microplate 301 is initially positioned in a precise first location where the microplate 301 is initially read by an optical detection system. The initial positioning should be repeatable such that removal of the microplate 301, manually or robotically, from the restraint mechanism 302 (for manipulation of the sample surfaces 304) should permit repositioning of the microplate 301 to a second location within the restraint mechanism 302 so that the first defined location differs from the second defined location by less than about 1 micron translation and less than about 4 arc seconds (4-5 arc seconds practicable, 3-4 arc seconds preferable, or 0-3 arc seconds even more preferred) or less than about 20 microRadians (preferably less than about 15 microRadians rotation). An optical detection system can then record a second measurement of the microplate sample surfaces 304 (and its contents) at the second defined location for analytical comparison with the initial first measurement. This repeatable positioning of the microplate 301 respective to the restraint mechanism 302 allows for more accurate instrumental interrogation of chemical or biological samples.

In drug discovery, for example, various types of biological or chemical material may be added to precise locations on a sample surface 304 (i.e. wells) of a microplate 301. The microplate 301 is capable of being interrogated by an optical reader positioned below the restraint mechanism 302 to produce an initial reading/result. When the microplate 301 is removed from its initial location, the sample surfaces 304 are manipulated (possibly by addition of a particular drug candidate). Additional measurements can comparatively be made with precision; as in a preferred embodiment, reinsertion of the microplate 301 into a second location of the restraint mechanism 302 as the sample surface 304 was initially read would be necessarily important. Specifically, the measurement results for each sample on the sample surfaces 304 can accurately be compared to determine possible binding or nonbinding of the drug to the particular biological or chemical molecules in each specific location of the surfaces 304. With the manipulation of smaller molecules on a micro-scale, accuracy in (re)positioning the microplate 301 becomes increasingly important. In a preferred embodiment involving analytical interrogation of a sample well having a sensor/grating incorporated in the bottom surface, it is critical to have a microplate positioned in an initial location that is a repeatable positioning to a same precise location with respect to an optical detector.

Further, the mating features 355 and microplate mating features 365 can be molded (or injecting molded), machined, glued, or attached in various other ways to the respective restraint mechanism 302 and/or microplate 301 so long as the attachments provide a rigid stable configuration for the microplate 301 to rest on the restraint mechanism 301. Additionally, the mating features 355 may be recessed into the base 303 to align with microplate mating structures 365 protruding from an underside of the microplate 301 to engage with the recessed mating features 355. As such, the mating features 355 of the restraint mechanism 301 and microplate mating features 365 can be comprised of a single geometric shape alone or in combination with multiple geometries so long as once engaged, the plate is held in a stable position. Such geometries may include conical, V-shaped, spherical, octagonal, rectangular, cylindrical, triangular shapes, or any other geometrical shapes. The shapes and/or configurations of the mating features 355 and microplate mating features 365 are listed for exemplary purposes only and not limitation. Multiple geometric arrangements are possible when three mating features 355 are capable of interacting with three microplate mating features 365 (six total contacts), including any combination or permutation of the following: a) three projecting spheres/balls against three V-shaped structures, b) three projecting spheres against one conical surface, one V-shaped structure, and one flat surface, c) three projecting spherical surfaces against two V-shaped structures and one flat surface, d) three projecting cylindrical surfaces against three V-shaped structures, or any other geometric projecting surface(s) against a mated counterpart, the mated counterpart having a single or combination of geometric surfaces.

Figure 4:
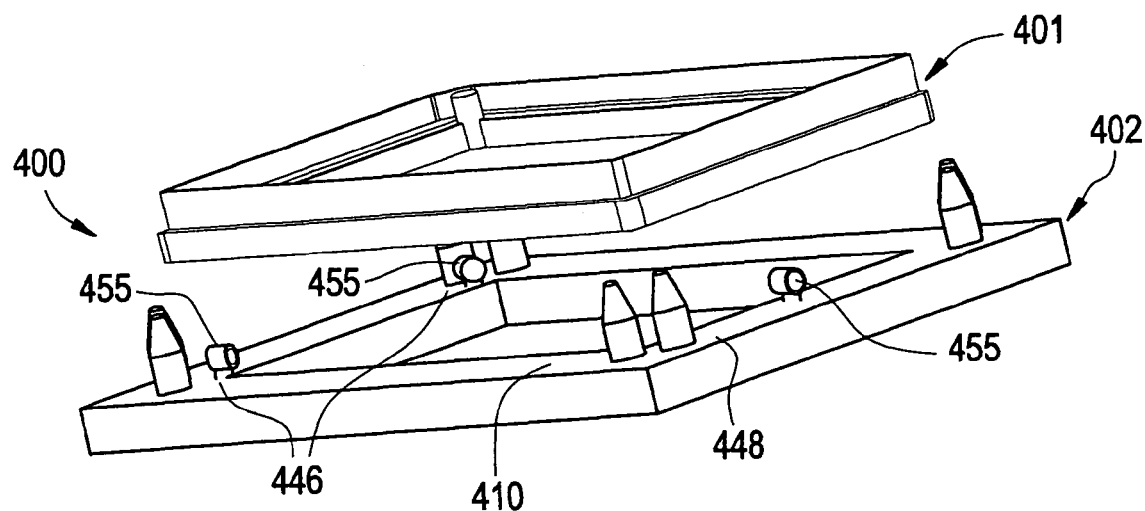
FIG. 4 is another illustrative embodiment of a microplate assembly.
Figure 4A:
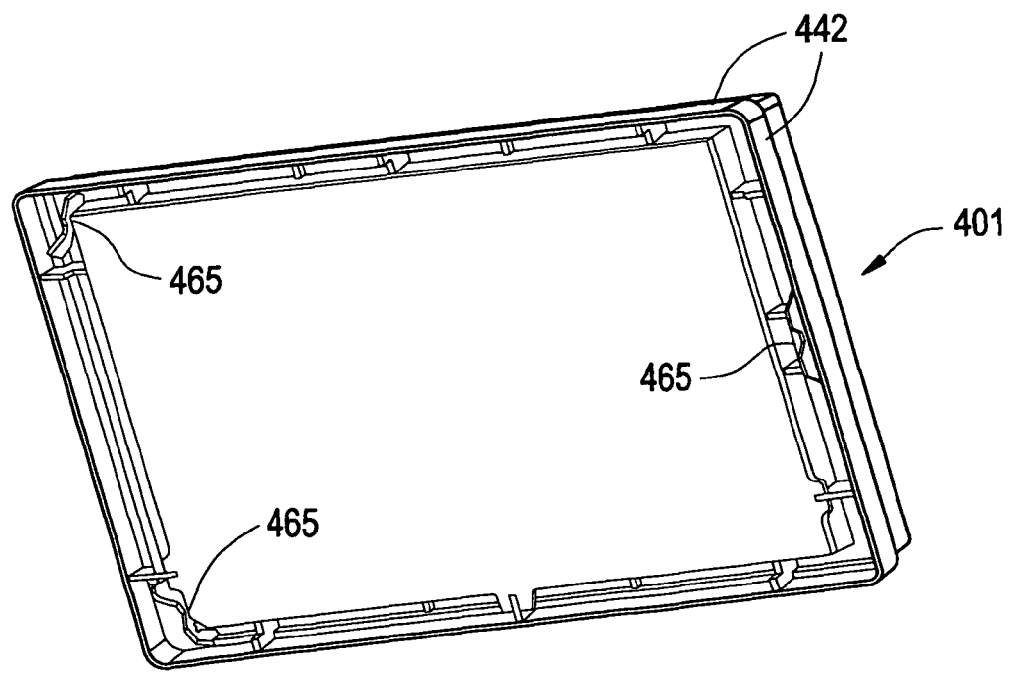
FIG. 4A is an underside perspective view of the detached microplate from FIG. 4.

Another embodiment of the present invention (FIG. 4) includes a microplate assembly 400 comprising microplate 401 being positioned within the restraint mechanism 402. The nesting receptacle of the restraint mechanism 402 has mating features/structures 455 capable of engaging with a microplate 401. The mating features 455 are cylindrical structures 455 protruding from the surface 410 of the restraint mechanism 402. As seen in FIG. 4A, the underside of a microplate 401 has microplate mating features 465 as microplate V-shaped recesses 465. The recesses 465 may be incorporated in a mold of the microplate, machined, or glued onto the underside of a microplate. In this preferred embodiment, an epoxy or other adhesive enables the fabrication of the recessed microplate mating features 465. The illustrative embodiment, however, is not limited to microplate V-shaped recesses 465 and can be a variety of shapes as discussed previously. In addition, the restraint mechanism 402 of the present invention is not limited to the mating structures 455 of the restraint mechanism 402 (and the corresponding microplate mating features 465 of the microplate 401) located in only two corners 446 and one end wall 448; any number of mating features 455 can be positioned elsewhere on the restraint mechanism 402 so that corresponding microplate mating features 465 of the microplate 401 are capable of engaging with the restraint mechanism 402. The microplate 401 of this assembly 400 is further capable of comprising an array of wells as discussed previously, each well having a sensor or grating located within a bottom surface of each well. The sensors or gratings of each well would preferably be capable of aligning with one or more optical beams. Contributory to this embodiment is an aperture included as part of the nest/nesting receptacle for analysis of a microplate from an underside; however, various other analytical techniques or methods that do not rely on optical viewing/analysis from below the plate would not necessitate an aperture. The mechanism can be engaged whenever restraint of a plate is required.

Although the kinematic mount/restraint mechanism described herein is generally intended for use with rectangular microplates, other shaped plates (oval, round, polygonal, etc.) may be similarly restrained. Additionally, a modified plate mounted using exact, kinematic constraints may not need any sidewalls or corners.

Figure 5:
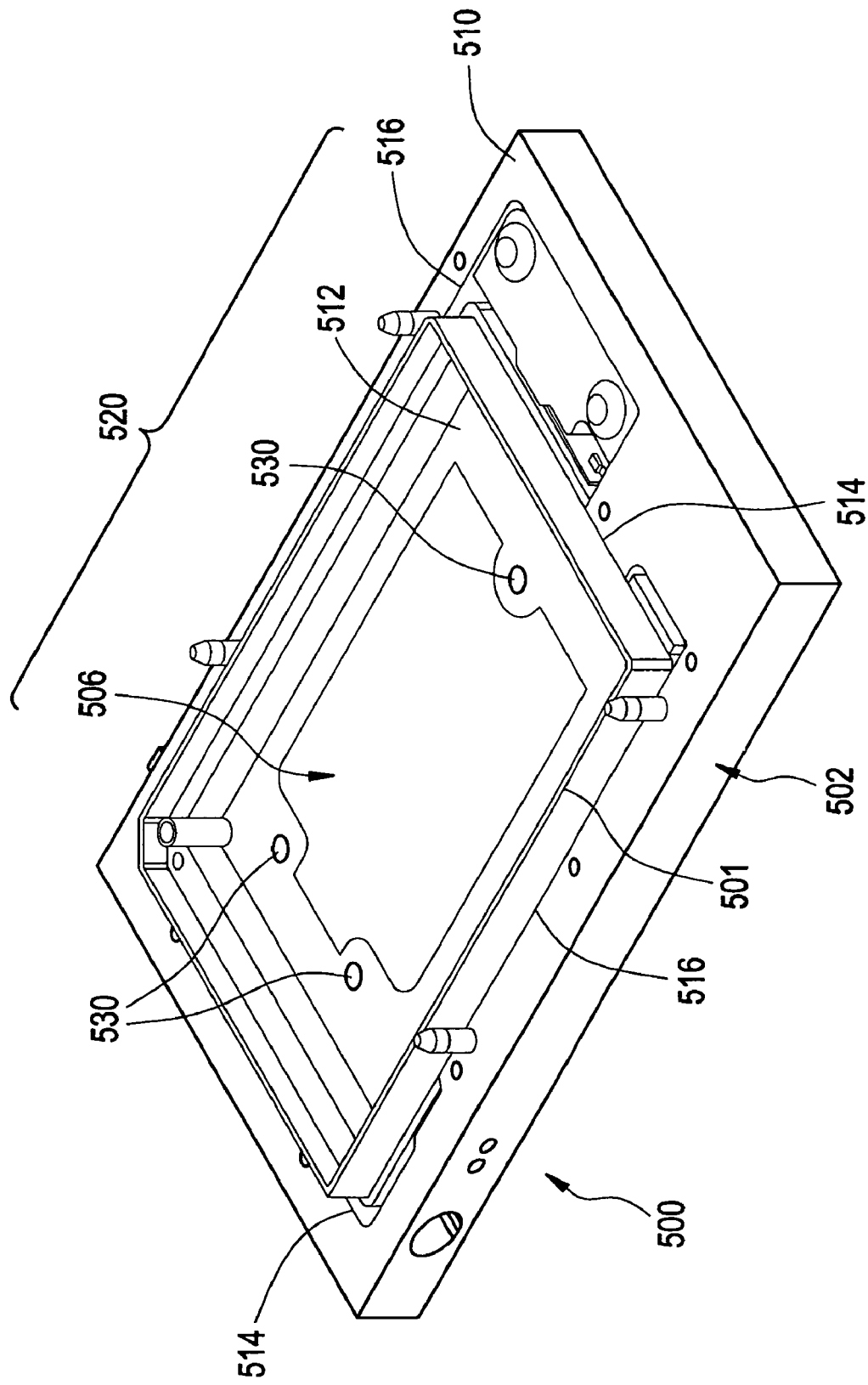
FIG. 5 is another preferred embodiment of the restraint mechanism utilizing a secondary surface.

Still another embodiment of the present invention is illustrated in FIGS. 5-5E. In this embodiment, the restraint mechanism 500 comprises a base 502 with two surfaces, one primary surface 510 and a secondary surface 512. Secondary surface 512 is inset on the end walls 514 and side walls 516 that form the opening/detection aperture 506 within the base 502. The secondary surface 512 forms a ledge 512, peripheral to the detection aperture 506, and defines a nesting receptacle 520. As in previous embodiments, the area occupied by a restrained microplate 501 forms the nesting receptacle 520 (as seen in a transparent top view of the restraint mechanism 500 in FIG. 5). The nesting receptacle 520 is defined by the location within the restraint mechanism 500 upon which a microplate is securely supported. The nesting receptacle 520 is further defined by the secondary surface 512 having three supports 530 capable of supporting and contacting a microplate 501 in the Z-directional plane. It is preferable, however, for the restraint mechanism 500 in this embodiment to have eight contact points to establish the position of a microplate in the X, Y, and Z planar directions as seen in a top view of a preferred restraint mechanism in FIG. 5A. The eight contact points in a preferred restraint mechanism 500 include: three supports 530 within the nesting receptacle 520 positioned in a triangular configuration and projecting from the surface 512, as well as five additional positioning structures, two contacts in the X-direction 540$x$ located on an end wall 514, one contact in the Y-direction 540$y$ located on a side wall 516, and two spring-loaded contacts 550$x$ and 550$y$ located on an opposite end wall 514 and a side wall 516, respectively opposing forces from the X-directional and Y-directional contacts, respectively. In this embodiment, the nesting receptacle 520 is inclusive of the five additional positioning structures as described. Adjustments 517 for each of these positioning contacts 540$x/y$ are located on an exterior surface 521 of the restraint mechanism 500. Leaf-spring adjustments 519 are utilized to adjust applicable spring forces. Such adjustments 517 or leaf-spring adjustments may be screws or alternative means for adjusting the forces applied to a microplate. Additional adjustments may be utilized to accommodate alternative microplate dimensions (i.e. adjustments for the heights of the supports 530).

Figure 5B:
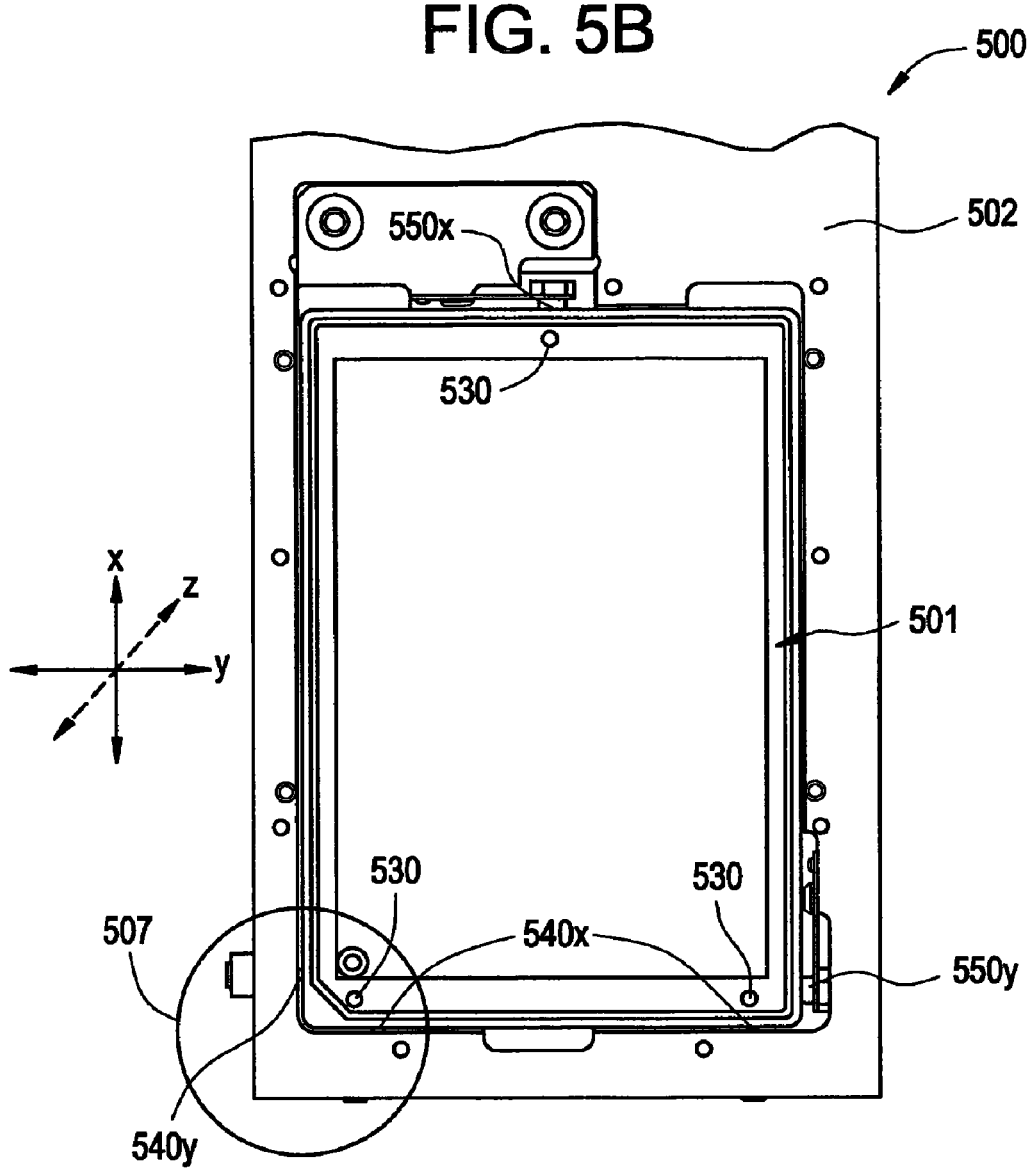
FIG. 5B is a top view of a microplate nested in the restraint mechanism.
Figure 5C:
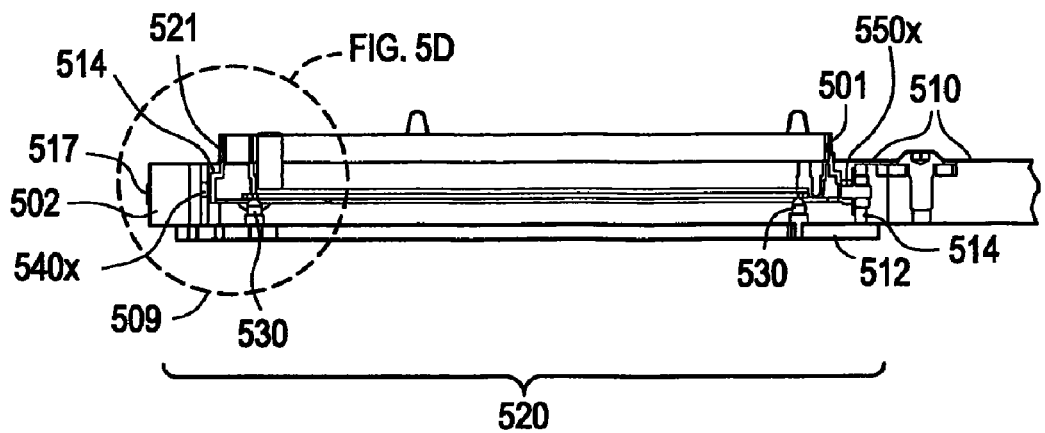
FIG. 5C is an enlarged cross-sectional view of FIG. 5A across section line b-b.
Figure 5D:
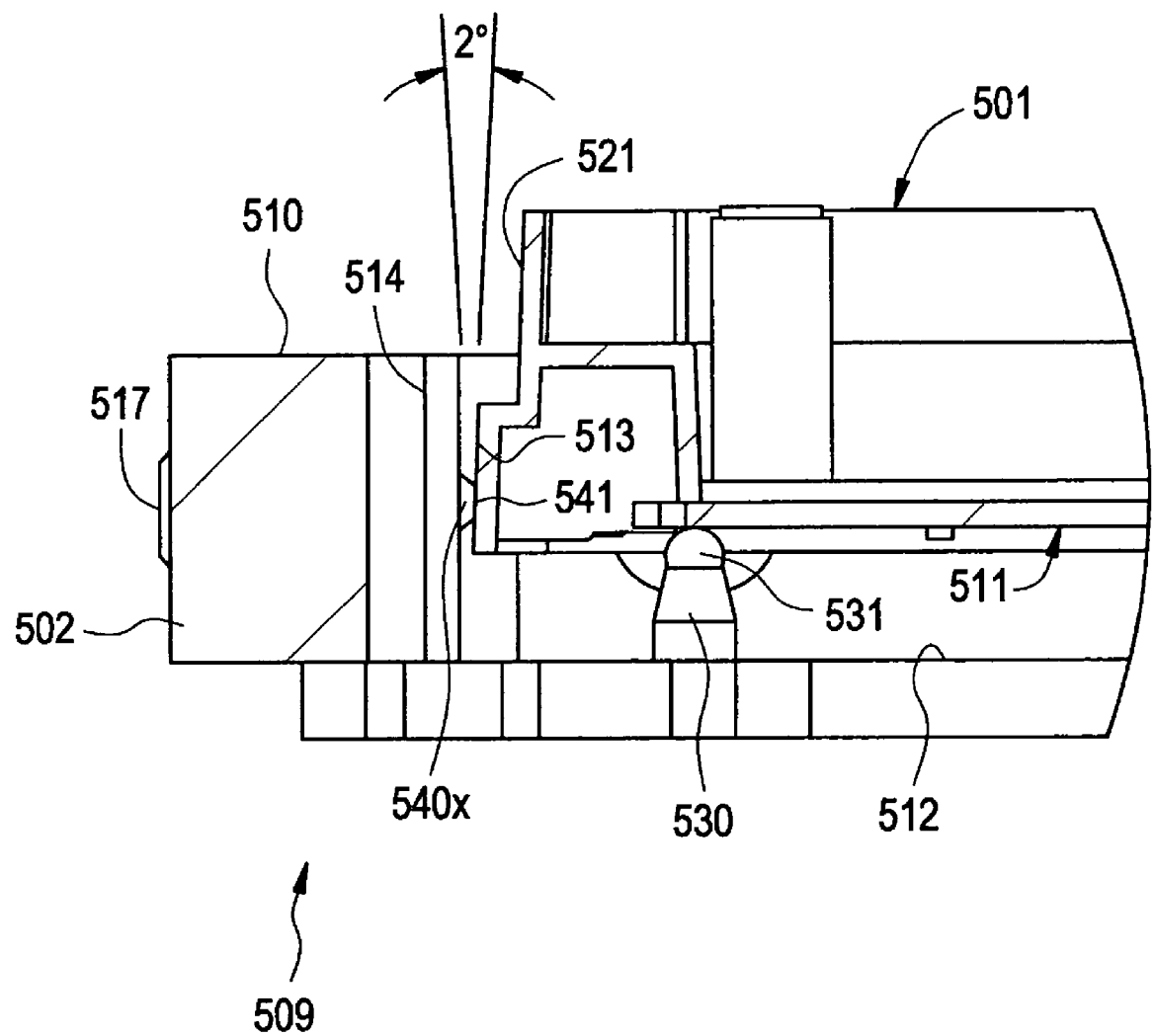
FIG. 5D is an enlarged partial cross-sectional view of corner 509 from FIG. 5C.

A transparent top view of the microplate 501 restrained in the mechanism 500 is seen in FIG. 5B. The microplate 501 is restrained by the following eight contact points: three supports 530 to establish the microplate sensor plane in the Z direction, three contacts 540$x$/540$y$ to establish the X-directional and Y-directional positions of a corner 507 of the microplate 501, and two spring-loaded contacts 550$x$ and 550$y$ to accommodate preload forces into locations of the X-directional contacts 540$x$ and Y-directional contacts 540$y$, respectively. A sectional cut across 5C-5C (from FIG. 5A) is revealed in an enlarged cross-sectional view of a microplate 501 restrained in the mechanism 500 in FIG. 5C. The spherical shaped supports 530, spherical shaped X-directional contact 540$x$, and spring-loaded contact 550$x$ contact a restrained microplate 501. The supports 530 stabilize and support the microplate 501 in the nesting receptacle 520 of the restraining mechanism 500. Typically, the supports 530 as well as the postioning structures 540$x$, 540$y$, 550$x$, and 550$y$ are composed of a hard, rigid, nonreactive material such as carbide. Furthermore, it is preferable to have spherical shaped supports 530 and spherical positioning structures 540$x/y$ and 550$x/y$ capable of point contacting the microplate 501. A spherical carbide ball 551 is incorporated on the leaf springs 550$x$ and 550$y$. A magnified corner 509 is illustrated in FIG. 5D to further demonstrate the point contact 531 of the support 530 contacting an underside surface 511 of the microplate 501. Additionally, the point contact 541 of the positioning structure 540$x$ contacts an exterior sidewall 513 (or flange) of the microplate frame/flange 521. Further, the exterior sidewall 513 typically has a draft angle of approximately two degrees. The draft angle is also accommodated by the applicable forces of the positioning structures 540$x/y$ and 550$x/y$ discussed previously, specifically shown by the Y-directional contact 540$y$ in the magnified illustration. These applicable forces, however, are capable of being adjusted to assist in mounting microplates having various sidewall draft angles. The reduced surface area of the contacts 540$x/y$, 550$x/y$, and 551 produces high loading per area and further generates normal forces (see transparent top view in FIG. 5E) to restrain a microplate 501. Though the surface area of the contact points 540x/y, 550x/y, and 551 is inherently reduced by their spherical shape, any shape may be utilized.

The positioning and restraint of the microplate 501 is explained in further detail by the applicable forces shown in FIG. 5E. For illustration purposes only, the microplate 501 is transparently viewed from a top viewpoint to explain its initial placement on the planar contacts 531. The microplate frame 521 can be inserted into the nesting receptacle 520 to initially contact and compress the spring-loaded contacts 550x/550y, followed by releasing the microplate 501 to gently contact the two stationary X contacts 540x and one Y contact 540y; the forces are distributed such that the microplate 501 can be positioned and repositioned, repeatedly, to the precise analytical location [first and second locations of which vary by less than about 1 micron translation and within less than about 20 microRadians rotation (preferably less than about 15 microRadians)]. As such, the force $F_{cy}$ from the Y-directional contact 540y is equilibrated by an opposing force $F_{sy}$ from the spring 550y. The forces $F_{c1x}$, $F_{c2x}$ from the X directional contacts 540x are equilibrated by an opposing force $F_{sx}$ from the spring 550x. In addition the spring-contacts 550x/550y have protruding spherical contact surfaces 551 to minimize contact with the microplate frame 521. Although one embodiment of the present invention may utilize leaf springs 550x/550y, other alternatives can use compression/coiled springs or alternative spring systems to counter the applied forces. Lighter spring forces from the spring-loaded contacts 550x and 550y, however, have demonstrated more repeatable positioning of the microplate 501, thereby generating more repeatable optical measurements.

Figure 6:
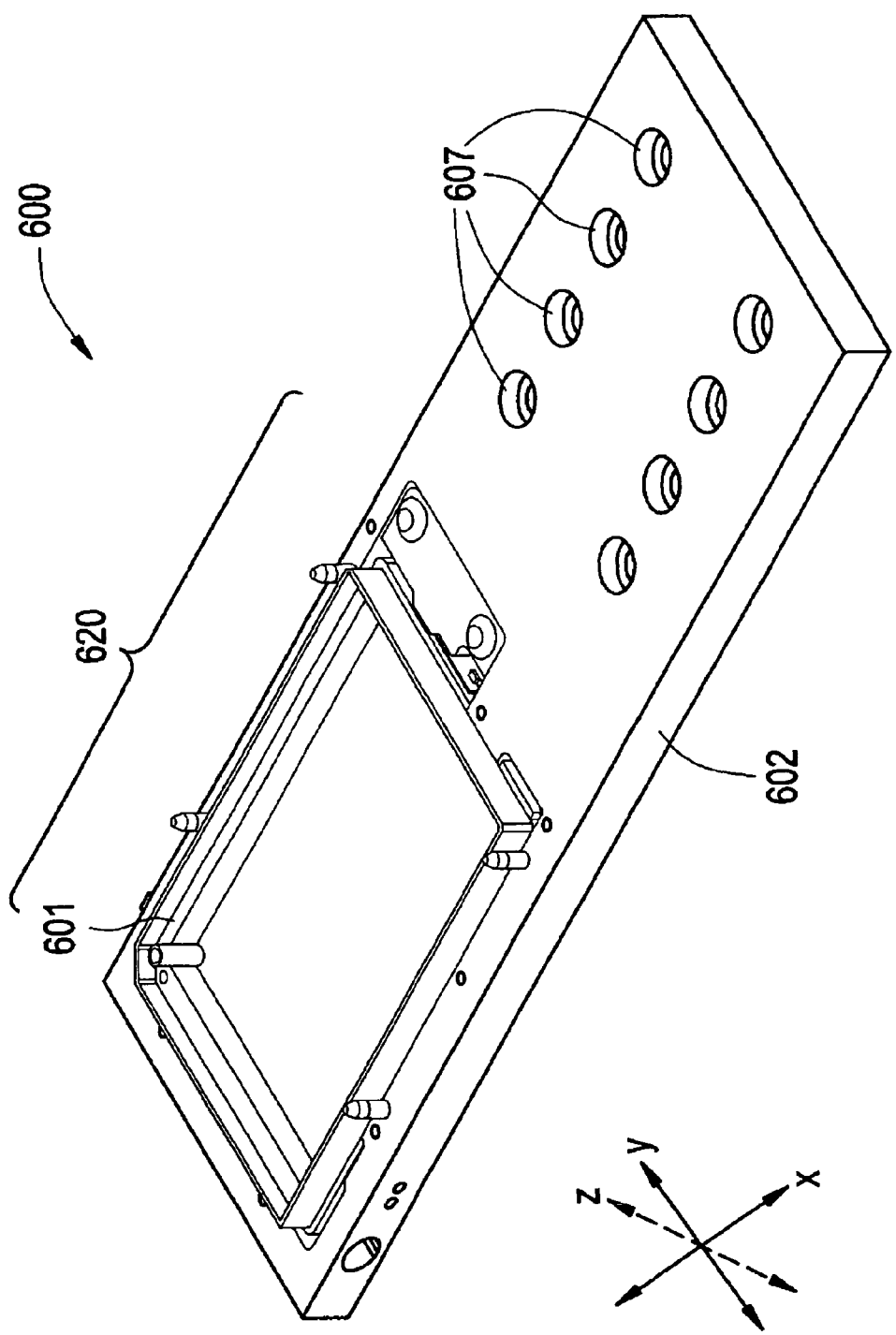
FIG. 6 is a restraint mechanism incorporated with features for attachment to a precision translation stage.

One embodiment of the present invention (FIG. 6) incorporates the restraint mechanism 600 mounted to a precision assembly or translation stage. The base 602 of the restraint mechanism 600 is utilized as a kinematic mount 600 whereby all six degrees of freedom are constrained by more than the anticipated six points of contact when a microplate 601 is inserted; "kinematic" referring to the active process of removing and reinserting the microplate 601 into view of an optical reader. As such, the kinematic mount 600 can easily be moved and relocated to a precise location above an optical detector. The restraining mechanism or kinematic mount 600 is secured to a precision assembly or translation stage (not shown) via the attachment spaces 607 allocated for screws or other means of attachment. The precision assembly acts as a structural assembly for support and stability of the restraint mechanism 600 further capable of restraining a microplate 601 in a restrained position of the nesting receptacle 620. A translation stage allows the restraint mechanism 600 holding a microplate 601 to move in X and Y planar directions above or below an optical detector or dispensing system, respectively, though alternative instrumental systems may be incorporated as well (above or below the restraint mechanism). Additionally, the translation stage could be modified to accommodate a Z planar directionality encompassing 3-dimensional movement of the restraint mechanism 600. For exemplary purposes only, not limitation, a precision assembly such as an air bearing is utilized to proficiently place the nesting receptacle 620 of the restraint mechanism 600 in alignment with an optical reader to within tenths of arc seconds. A preferred embodiment of this invention includes the air bearing (using pressurized air) to control movement of the restraint mechanism 600 back and forth across an optical detection system wherein the nesting receptacle 620 holding the microplate 601 can be precisely positioned to a location above an optical reader/detector. Thereafter, the microplate 601 can be repeatably inserted to a first location, removed, and reinserted to an analagous second location of the nesting receptacle 620, each location within less than about 1 micron translation and less than about 20 microRadians rotation in angle/pitch/roll of each other.

Additionally, this embodiment does not require a specifically modified microplate, and can be employed with standard, off-the-shelf plates currently utilized throughout the art. In fact, the extra contact points in this embodiment [eight contacts in comparison with six contacts discussed in a previous embodiment] are exemplary for the utilization of standard microplates. Furthermore, a preferred embodiment of the restraint mechanism 600 of the present invention is shaped and configured to enable robotic access to the base 602 of the restraining mechanism 600, where the microplate 601 is positioned into the nesting receptacle 620 of the base 602 without requiring cumbersome robotic arm manipulation.

Alternatively, restraint mechanisms may be stationary while the optical components have mobility above or below the restraint mechanism. The invention, therefore, is not limited to the utilization of an optical detection system below a microplate and may be utilized in any apparent system requiring restraint or immobilization of a microplate. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

The invention claimed is:

1. A mechanism for positionally restraining a microplate comprising: a base, said base having at least one surface defining a nesting receptacle for said microplate, and three supports projecting from said base, said supports contact an underside surface of said microplate to support said microplate in a Z-directional plane, said nesting receptacle has at least two side walls and at least two end walls, said nesting receptacle further has two X-directional contacts and one Y-directional contact respectively located on one of said end walls and one of said side walls, said nesting receptacle also has at least one spring-loaded contact on said end wall opposite said X-directional contacts and at least one spring-loaded contact on said side wall opposite said Y-directional contact, where the two X-directional contacts and the one Y-directional contact establish X-directional and Y-directional positions of a corner of said microplate.

2. The mechanism as set forth in claim 1, wherein said nesting receptacle has the at least two side walls and the at least two end walls that intersect in corners to form a rectangular shape, said walls further defining a detection aperture thereby allowing optical access to at least one surface of said microplate through said detection aperture.

3. The mechanism as set forth in claim 1, wherein said supports are composed of nonreactive materials inclusive of ceramic, carbide and/or metallic compositions.

4. The mechanism as set forth in claim 1, further comprising a precision assembly, said base secured to said precision assembly.

5. The mechanism as set forth in claim 2, said supports further comprising one or more mating feature(s) capable of interacting with one or more microplate mating feature(s).

6. The mechanism as set forth in claim 5, wherein at least one guide pin is located on a periphery of said nesting receptacle capable of aligning said microplate with said supports.

7. The mechanism as set forth in claim 6, whereby one or more set(s) of guide pins are located on said corners of said nesting receptacle such that said guide pins are capable of aligning at least one microplate corner.

8. The mechanism as set forth in claim 7, said guide pins having a cylindrical shape at a point of attachment on said periphery tapering upward to a conical shape whereby a frame of said microplate is capable of being received.

9. The mechanism of claim 5, wherein said mating features are a single geometry or combination of multiple geometries, further comprising conical, V-shaped, spherical, octagonal, cylindrical, or any geometric shape.

10. The mechanism of claim 5, wherein three said mating features are capable of interacting with three said microplate mating features in multiple geometric arrangements including any permutation of the following:
three projecting spheres against three V-shaped structures,
three projecting spheres against one conical surface, one V-shaped structure, and one flat surface,
three projecting spherical surfaces against two V-shaped structures and one flat surface, or
three projecting cylindrical surfaces against three V-shaped structures.

11. The mechanism as set forth in claim 1, wherein said two X-directional contacts, said one Y-directional contact, and said spring-loaded contacts are positioned in a plane parallel to and at or above the Z-directional plane.

12. A microplate assembly comprising:
a restraint mechanism having a base, said base having at least one surface defining a nesting receptacle for a microplate, and at three supports projecting from said base, said supports contact an underside surface of said microplate to support said microplate in a Z-directional plane, said nesting receptacle has at least two side walls and at least two end walls, said nesting receptacle further has two X-directional contacts and at one Y-directional contact respectively located on one of said end walls and one of said side walls, said nesting receptacle also has at least one spring-loaded contact on said end wall opposite said X-directional contacts and at least one spring-loaded contact on said side wall opposite said Y-directional contact, where the two X-directional contacts and the one Y-directional contact establish X-directional and Y-directional positions of a corner of said microplate; and
said microplate located within said nesting receptacle, said microplate comprising a substantially flat transparent lower plate having at least one bottom surface for an array of sample wells, a unitary upper plate forming sidewalls for the sample wells, said sample wells surrounded by a frame.

13. The microplate assembly of claim 12, said microplate further comprising at least one sensor within said bottom surfaces of at least one said well, said sensors capable of aligning with one or more optical beams.

14. The mechanism as set forth in claim 2, said nesting receptacle having one or more secondary surface(s), wherein said supports project from said secondary surface.

15. The mechanism as set forth in claim 14, said secondary surface(s) inset on said end walls and said side walls forming a ledge on a periphery of said detection aperture, wherein said supports include one or more point contact(s).

16. The microplate assembly as set forth in claim 12, wherein said two X-directional contacts, said one Y-directional contact, and said spring-loaded contacts are positioned in a plane parallel to and at or above the Z-directional plane.

17. The mechanism of claim 1, further comprising one or more adjustment(s) to position said microplate to include: one or more X-directional contact adjustment(s), one or more Y-directional contact adjustment(s), one or more spring-loaded adjustment(s), and/or at least one adjustment for said supports.

18. A method for positionally restraining a microplate, said method comprising:
providing a base, said base having at least one surface defining a nesting receptacle for said microplate, and three supports projecting from said base, said supports contact an underside surface of said microplate to support said microplate in a Z-directional plane, said nesting receptacle has at least two side walls and at least two end walls, said nesting receptacle further has at least two X-directional contacts and one Y-directional contact respectively located on one of said end walls and one of said side walls, said nesting receptacle also has at least one spring-loaded contact on said end wall opposite said X-directional contacts and at least one spring-loaded contact on said side wall opposite said Y-directional contact, where the two X-directional contacts and the one Y-directional contact establish X-directional and Y-directional positions of a corner of said microplate;
providing said microplate comprising: a substantially flat transparent lower plate having at least one bottom surface for a plurality of sample wells, a unitary upper plate forming sidewalls for the sample wells, said plurality of sample wells surrounded by a frame,
providing an optical detection system, and
inserting said microplate within said nesting receptacle, said microplate occupying a first defined location.

19. A method as in claim 18, further comprising:
removing said microplate from said nesting receptacle, and reinserting said microplate within said nesting receptacle at a second defined location, said second defined location varying from said first defined location by less than about 1 micron translation and less than about 4 arc seconds or 20 microRadians rotation.

20. The method as set forth in claim 18, wherein said two X-directional contacts, said one Y-directional contact, and said spring-loaded contacts are positioned in a plane parallel to and at or above the Z-directional plane.

* * * * *